United States Patent [19]

Clark

[11] Patent Number: 4,815,462

[45] Date of Patent: Mar. 28, 1989

[54] LIPECTOMY DEVICE

[76] Inventor: Vickie J. Clark, 7601 Weldon Ave., Bakersfield, Calif. 93308

[21] Appl. No.: 34,598

[22] Filed: Apr. 6, 1987

[51] Int. Cl.⁴ ............................................. A61F 17/32
[52] U.S. Cl. .................................... 128/305; 604/902; 128/304; 128/752
[58] Field of Search ....................... 128/305, 304, 33.1, 128/750–752, 755, 758, 303.17, 303.14; 604/902, 35, 22

[56] References Cited

U.S. PATENT DOCUMENTS

| 3,082,805 | 12/1960 | Royce | 128/755 |
| 3,732,858 | 5/1973 | Banko | 128/305 |
| 3,828,780 | 8/1974 | Morrison, Jr. | 604/902 |
| 4,061,146 | 12/1977 | Baehr et al. | 604/22 |
| 4,167,943 | 9/1979 | Banko | 604/22 |
| 4,589,414 | 5/1986 | Yoshida et al. | 604/22 |
| 4,606,342 | 8/1986 | Zamba et al. | 128/303.17 |
| 4,729,763 | 3/1988 | Henrie | 128/305 |

FOREIGN PATENT DOCUMENTS 1441549  7/1976  United Kingdom ........... 128/303.14

*Primary Examiner*—Stephen C. Pellegrino
*Assistant Examiner*—Colleen Reilly
*Attorney, Agent, or Firm*—Henry M. Bissell

[57] ABSTRACT

The lipectomy device includes a generally hollow tubular housing to the open front end of which are releasably sealingly connected an elongated hollow tubular suction conduit, with a rounded closed front end bearing at least one opening, and a cutting blade with the shaft and cutting tip thereof wholly disposed in the conduit and spaced inwardly therefrom. The cutting blade is releasably connected to an electrical motor in the housing for rotation of the blade, and a suction line also runs into the front end of the housing to remove severed tissue sucked through the blade and/or conduit. The device may include an electrocoagulation component which includes the blade tip in the form of electrically resistive metal, and an electrical circuit between a housing switch, the blade tip and an external electrical power source. The device is compact, portable and efficient in removing lipoidal tissue by suction, with excision thereof by the blade tip as it rotates in the conduit and also providing electrocoagulation, as needed, by the blade tip of small blood vessels to avoid hematomas.

9 Claims, 2 Drawing Sheets

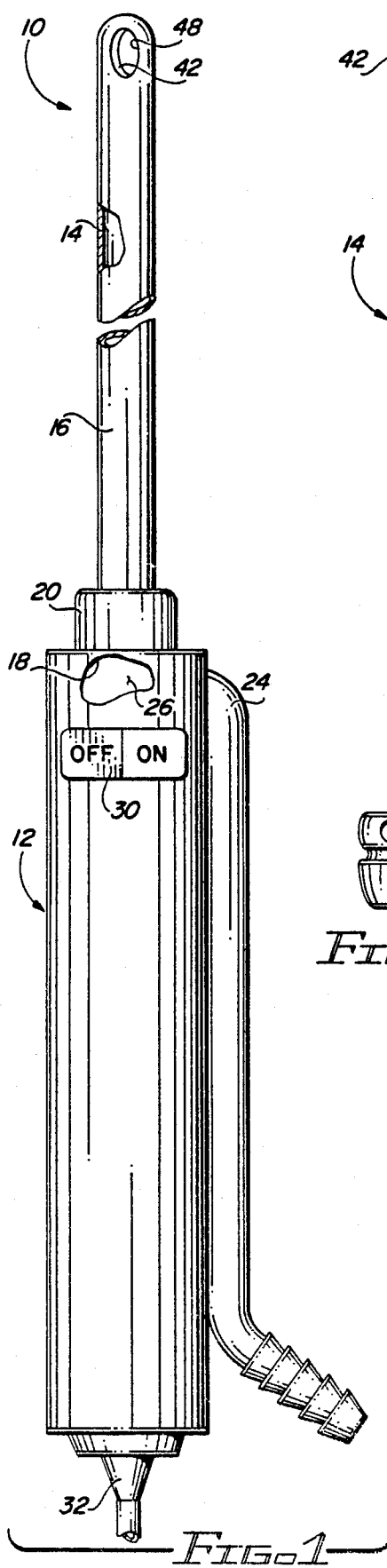
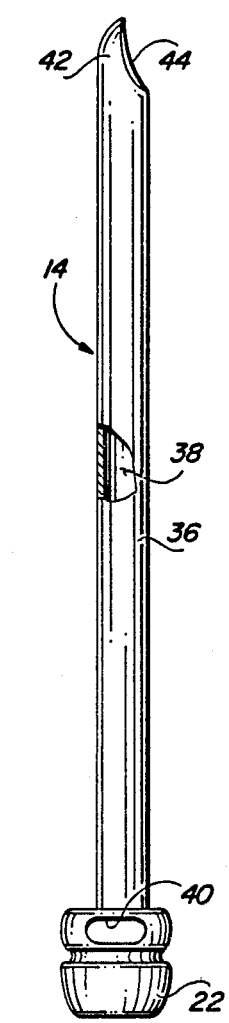
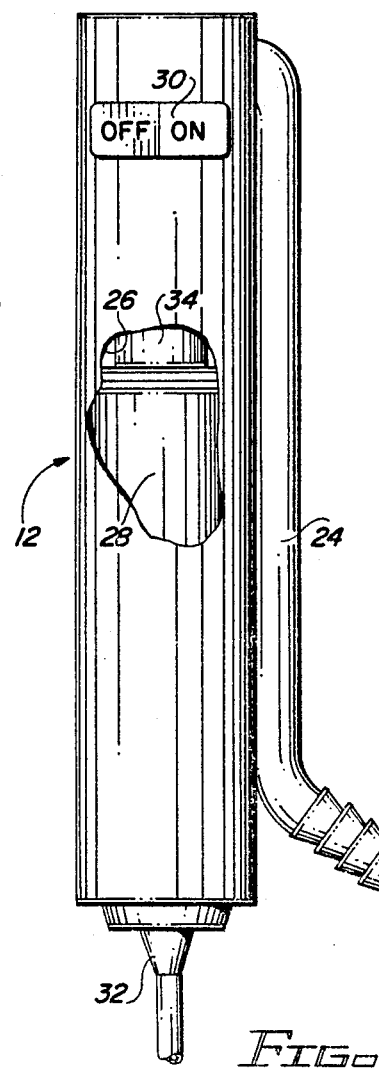

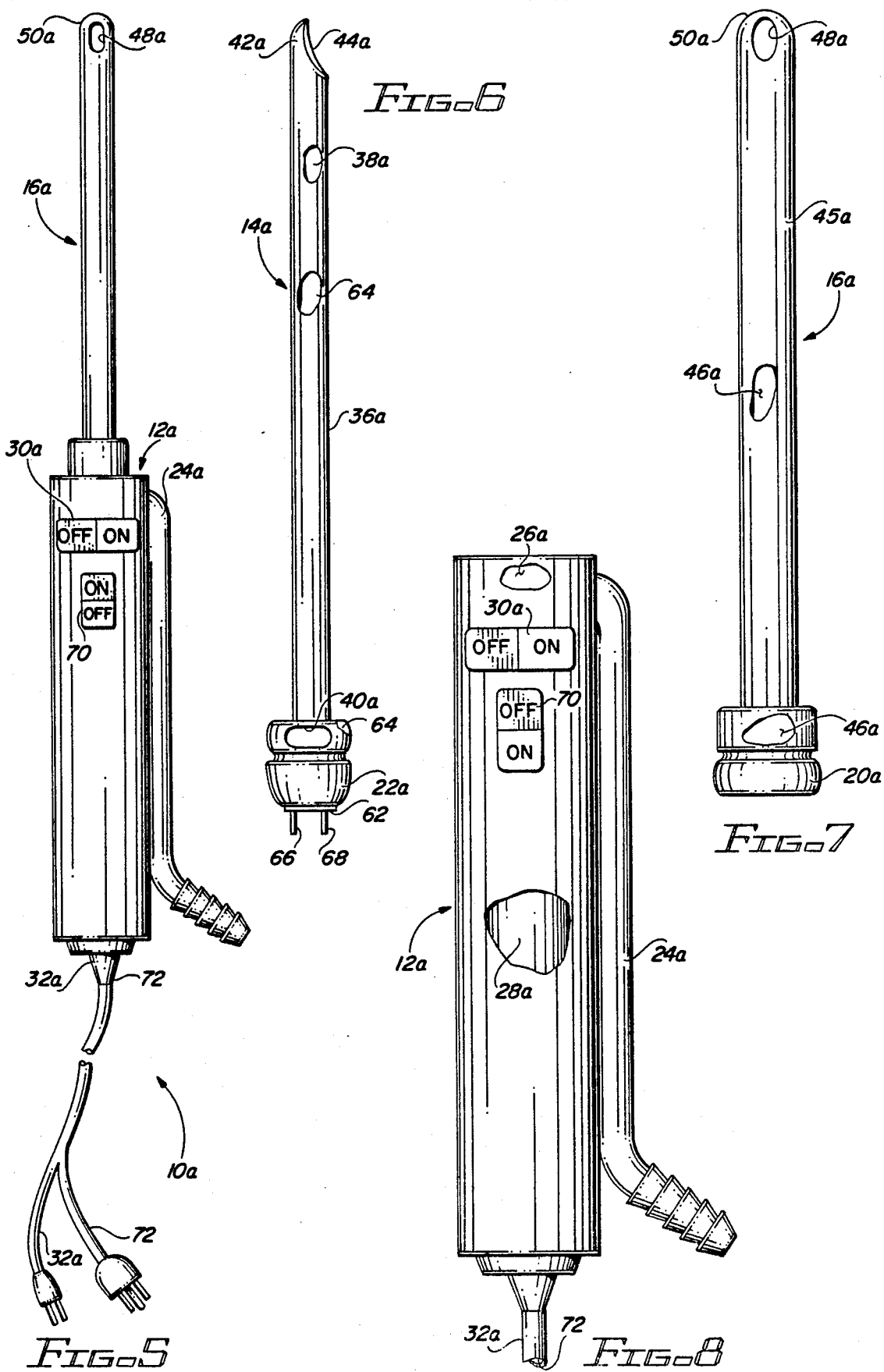

LIPECTOMY DEVICE

BACKGROUND OF THE INVENTION

1. Field of the Invention

The present invention generally relates to medical instruments and, more particularly, to an improved lipectomy device.

2. Background.

Suction lipectomies are surgical procedures carried out to remove excess adipose tissue from the body for improved cosmetic appearance and as an aid in certain life-threatening situations. In the conventional lipectomy procedure, the surgeon inserts a suction cannula, which is a hollow tube connected to a suction source, under the skin and then moves the cannula tip back and forth so that it can break away fat globules which are then sucked into the cannula and away from the body. This procedure is crude and requires much time and effort on the part of the surgeon. It can result in extensive bruising of body tissues, the development of massive hematomas, etc. There is also the real danger of dislodging pieces of fat which are not subsequently suctioned away by the cannula but which can later be picked up by the blood stream and cause an embolism, with potentially fatal results.

Rotating cutting blades heretofore utilized for small surgical procedures such as arthroscopic surgery have not been employed for lipectomies. Usually, such cutters do not have suction cannulas associated therewith and if such are associated, the suction is weak and the blade tips are left exposed in order to render them useful in directly cutting cartilage, bone fragments and the like.

There remains a need for an improved lipectomy device which will quickly break up and fully remove human adipose body tissue without creating a danger of developing hematomas and embolisms. Such a device should be simple, compact, portable, durable and efficient. It should be capable of rapidly achieving hemostasis at the surgery site with a minimum of effort and difficulty.

SUMMARY OF THE INVENTION

The improved lipectomy device of the present invention satisfies all the foregoing needs. The device is substantially as set forth in the Abstract. Thus, it includes a hollow housing, to the open front end of which are releasably sealingly connected an elongated tubular conduit with central passageway and a rounded closed front end, the latter bearing a lateral opening, and a cutting blade. An external suction line is also connected to the housing front end. The blade shaft and cutting tip thereof are disposed wholly in the passageway, and the shaft is connected to an electrical motor in the housing, for rotation of the shaft and tip within the conduit. The blade, shaft and tip may be hollow and may be connected to suction, as is the conduit.

Thus, the conduit prevents the blade tip from direct cutting of the adipose tissue outside the conduit. Instead, it does not cut the adipose tissue until it is sucked into the conduit through the lateral opening. This eliminates the possibility of bits of adipose tissue being torn loose and not sucked up, with subsequent possible embolisms. Moreover, the cutting blade does not inadvertently inflict damage on blood vessels and other non-adipose organs during the surgery, yet greatly enhances the rate and efficiency of the lipectomy.

In one embodiment, the housing, conduit and blade, except for its tip, are electrically insulated. The tip is electrically resistive metal and is part of an electrocoagulation unit which includes an electrical circuit to the tip for electrocoagulation of tissue, blood vessels and the like, as desired, to reduce surgical injury, prevent hematomas and promote rapid hemostasis. Such electrocoagulation unit has the circuit connected to an on-off switch in the housing and may also be connectable to an external electrical power source, such as a suitably fault-protected circuit.

BRIEF DESCRIPTION OF THE DRAWING

A better understanding of the present invention may be realized from a consideration of the following detailed description, taken in conjunction with the accompanying drawing in which:

FIG. 1 is a schematic top plan view, partly broken away, of a first preferred embodiment of the improved lipectomy device of the present invention;

FIG. 2 is a schematic top plan view, partly broken away, of the cutting blade of the device of FIG. 1;

FIG. 3 is a schematic top plan view, partly broken away, of the suction conduit (blade sheath) of the device of FIG. 1;

FIG. 4 is a schematic top plan view, partly broken away, of the housing of the device of FIG. 1;

FIG. 5 is a schematic top plan view of a second preferred embodiment of the improved lipectomy device of the present invention;

FIG. 6 is a schematic top plan view, partly broken away, of the cutting blade of the device of FIG. 5;

FIG. 7 is a schematic top plan view, partly broken away, of the suction conduit (blade sheath) of the device of FIG. 5; and FIG. 8 is a schematic top plan view, partly broken away, of the housing of the device of FIG. 5.

DETAILED DESCRIPTION

FIGS. 1-4:

Now referring more particularly to FIGS. 1-4, a first preferred embodiment of the improved lipectomy device of the present invention is schematically depicted therein. Thus, device 10 is shown which comprises a hollow housing 12 to which are releasably connected a rotatable cutting blade 14 and a suction conduit 16. Blade 14 is adapted to be reasably sheathed in suction conduit 16.

Housing 12 is generally hollow and tubular, for example, about 3 cm. in diameter and 19 cm. long, and can be fabricated of metal, plastic, rubber, ceramic or the like. It has an open front end 18 in which rear coupler 20 of conduit 16 and rear fitting 22 of blade 14 are releasably disposable, as shown in FIG. 1, to releasably seal front end 18 A suction line 24 communicates with the central cavity 26 in front end 18 and extends outwardly of housing 12 for releasable connection with a suction source. Housing 12 has power means in the form of an electrical motor 28 disposed in cavity 26 and connected to an "on-off" control switch 30 on the exterior of housing 12 and to an electrical lead 32 connectable to an electrical power source such as house current. It will be understood that motor 28 could be battery powered from batteries mounted externally or internally, if desired.

When blade 14 is seated with rear fitting in front end 18, it is connected by a coupling 34 in housing 12 to motor 28 for rotation of blade 14 around its longitudinal axis. Blade 14 comprises an elongated hollow tubular shaft 36, for example, about 15.3 cm. long and 8 mm. wide, having a central space 38 along the length thereof. The rear end of shaft 36 is connected to fitting 22 which may be, for example, about 2 cm. long and 2 cm. wide and which has an opening 40 therein communicating with space 38.

Space 38 extends up to and including cutting tip 42. Tip 42 may be, for example, about 1.5 cm. long and is sharp, curved toward the longitudinal center line of shaft 36 and has an opening 44 to receive cut tissue and to allow it to pass under suction into and through communicating space 38 for exiting from opening 40 into cavity 26 and thence exiting device 10 through suction line 24. Tip 42 is preferably affixed to the shaft 36 and is of stainless steel or the like. Shaft 36 may also be metal or other suitable material, as can fitting 22.

Blade 14 releasably fits into elongated hollow tubular cylindrical conduit 16 which may be, for example, 17 cm. in overall length and acts as a protective sheath for blade 14. Conduit 16 has a hollow tubular portion 45, for example, about 15 cm. long and 10 mm. wide with a central passageway 46 extending the length thereof and communicating with the exterior through one or more openings 48 in otherwise closed round tip 50 thereof. Passageway 46 extends through coupling 20, which may be, for example, 2 cm. long and about 2 cm. wide so that when conduit 16 is connected, as a slip fitting, into end 18 of housing 12, passageway 46 is in communication with cavity 26 and suction is provided to passageway 46 through line 24.

When blade 14 is releasably disposed in conduit 16, as in FIG. 1, shaft 36 is spaced inwardly from the sidewall of conduit 16 in passageway 46, with fitting 22 below coupling 20 and attached to the drive motor shaft for rotation of blade 14 while conduit 16 is held stationary on housing 12. Opening 40 allows excised adipose tissue to pass from opening 40 into passageway 26 in the housing (FIG. 1) and then into the tube 24.

It will be understood that blade 14 and conduit 16 could be dimensioned so that fitting 22 would be behind coupling 20 in the assembled state. In that case, opening 40 would communicate directly with space 26.

Tip 42 in the operative position is within end 50 and adjacent opening(s) 48 and rotates rapidly therein so as to receive adipose tissue from opening 48 and instantly excise it and pass it under suction down through space 38.

When device 10 is assembled, as shown in FIG. 1, conduit 16 can be inserted under the skin by the surgeon and suction can be activated by connecting line 24 to a suction source. Switch 30 is turned on to cause blade tip 42 to rotate in end 50. The surgeon moves end 50 from one adipose area to another while suction is applied in space 38 and passageway 46 to draw bits of adipose tissue into opening(s) 48 and into contact with tip 42 for excision and rapid passage through space 38 to line 24 and out device 10. Since tip 42 is shielded by end 50, various organs and blood vessels are not inadvertently cut so that surgical trauma is minimal and the lipectomy can be conducted safely and rapidly for optimal results.

FIGS. 5-8:

A second preferred embodiment of the improved lipectomy device of the present invention is schematically depicted in FIGS. 5-8. Thus, device 10a is shown. Components thereof similar to those of device 10 bear the same numerals but are succeeded by the letter "a". Device 10a is substantially identical to device 10 except that it also includes an electrocoagulation unit in addition to the suction and cutting components.

Device 10a includes housing 12a having suction line 24a running into space 26a in which conduit 16a with blade 14a disposed therein are releasably sealingly connected. Tip 42a is affixed to shaft 36a and is disposed within front end 50 of conduit 16a adjacent opening(s) 48a. Shaft 36a has space 38a leading to opening 40a in fitting 22a and to opening 44a in tip 42a.

Fitting 22a has electrical conduit lead connectors in the form of rings 60 and 62 which extend as separate leads (not shown) up the inside of fitting 22a and shaft 36a to tip 42a which is of electrically resistive metal so that it heats to an elevated temperature when electrical current is passed therethrough.

The inner and outer surfaces of shaft 36a and fitting 22a bear an electrically insulative layer 64 to protect blade 14a. Conduit 16a and housing 12a are of electrically insulative material or coated therewith on all surfaces requiring insulation. Ring connectors 60 and 62 brush connect to electrical leads 66 and 68 which are part of an electrical circuit which interconnects tip 42a with an "on-off" switch 70 adjacent switch 30a (which controls electrical motor 28a) on the exterior of housing 12a and which runs to an external electrical power source (not shown) through double electrical lead lines 32a and 72 exiting housing 12a and which subsequently bifurcate. Line 32a interconnects with motor 28a to cause rotation of blade 14a while line 72 interconnects with tip 42a and is part of the electrocoagulation unit described above.

Tip 42a, when heated by turning switch 70 on, is used to heat seal any blood vessels inadvertently cut during the lipectomy, so as to prevent hematomas and promote hemostasis. Device 10a has the advantages of device 10, plus the desirable electrocoagulation feature.

Although there have been described above specific arrangements of an improved lipectomy device in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An improved lipectomy device, said device comprising, in combination:

(a) an elongated generally tubular suction conduit having a central passageway extending the length thereof, a rounded generally closed front end with at least one opening therein extending into said passageway, and a rear coupler;

(b) an elongated cutting blade releasably secured to said conduit in said passageway, and a front cutting tip adjacent said conduit front end and wholly within said passageway, said blade including a rear fitting;

(c) a tubular housing having an open front end communicating with a central cavity therein, a suction line connected to said central cavity in said front end and extending exterior of said housing for connection with a suction source, coupling means releasably connected to said rear coupler and said rear fitting for releasably sealingly securing said blade and said conduit in said housing front end to close the same, with said blade shaft and tip disposed in said conduit, and drive means in said housing releasably connected to said blade for rotation thereof in said conduit; and (d) electrocoagulation means connected to said blade tip, the blade tip being electrically conductive.

2. The improved lipectomy device of claim 1 wherein said blade shaft is hollow along the length thereof for transfer under suction of excised tissue therein to said housing front end and therefrom by said suction line.

3. The improved lipectomy device of claim 2 wherein said drive means comprises a switch-operated electrical motor in said housing.

4. The improved lipectomy device of claim 3 wherein said blade rear fitting includes a port communicating with said housing central cavity through said conduit passageway.

5. The improved lipectomy device of claim 4 wherein said blade tip is curved toward the longitudinal midline of said blade shaft and wherein said electrical motor is connectable to an external power source and is connected to an on-off switch on the exterior of said housing.

6. The improved lipectomy device of claim 4 wherein said conduit rear coupler is frictionally engageable with said housing front end and wherein said blade rear fitting is at least partially receivable within said rear coupler.

7. The improved lipectomy device of claim 1 wherein said blade shaft is electrically conductive and is electrically connected to said electrocoagulation means, the exterior of said blade shaft having an electrically insulative coating and wherein said conduit and housing are electrically insulative.

8. The improved lipectomy device of claim 7 wherein said electrocoagulation means includes an electrical circuit connected to said shaft and to an on-off switch on the exterior of said housing and extending out of said housing for connection to an electrical current source, and wherein said blade tip comprises an electrically resistive heating element.

9. The improved lipectomy device of claim 8 wherein said blade shaft is hollow along the length thereof for transfer of excised tissue by suction to and from said housing front end, and wherein said drive means comprises a switch-operated electrical motor in said housing connectable to an external electrical power source.

* * * * *